United States Patent [19]

Sugimoto et al.

[11] 3,954,826
[45] May 4, 1976

[54] PROCESS FOR PRODUCING α-SULFOPHENYLACETIC ACID DERIVATIVES

[75] Inventors: Keiichi Sugimoto, Kawani; Koji Nishijima, Osaka; Hiroshi Akimoto, Hyogo; Tadashi Hanaoka, Osaka; Nobuharu Kakeya, Kawani, all of Japan

[73] Assignee: Takeda Chemical Industries, Ltd., Osaka, Japan

[22] Filed: July 9, 1974

[21] Appl. No.: 486,835

[30] Foreign Application Priority Data

July 9, 1973  Japan................................ 48-77262
July 13, 1973 Japan................................ 48-79606
July 30, 1973 Japan................................ 48-85661

[52] U.S. Cl......................... 260/456 R; 260/239.1; 424/271
[51] Int. Cl.²...................................... C07C 143/68
[58] Field of Search.......... 260/456 P, 456 A, 456 R

[56] References Cited
UNITED STATES PATENTS

2,845,448  7/1958  Taylor............................. 260/456 P

FOREIGN PATENTS OR APPLICATIONS

1,298,088  11/1972  United Kingdom............ 260/456 P

OTHER PUBLICATIONS

Morimoto et al., J. Med. Chem., 15, pp. 1105-1108 (1972).
Stirton, J., Am. Oil Chem. Soc., 39, 490 (1962).
Wagner et al., "Synthetic Org. Chem.," pp. 480-483, 822-825 (1953).
Cohen et al., J. Amer. Chem. Soc., 63, 3382 (1941).
Lichtenberger et al., Bull. Soc. Chim. France, pp. 995-1001 (1948).
Abramovitch et al., J. Am. Chem. Soc., 65, 986 (1943).

*Primary Examiner*—James O. Thomas, Jr.
*Assistant Examiner*—Nicky Chan
*Attorney, Agent, or Firm*—Wenderoth, Lind & Ponack

[57] ABSTRACT

α-Sulfophenylacetic acid derivatives of the general formula:

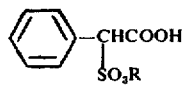

(wherein R is a substituted or unsubsituted primary alcohol, cyclic alcohol or phenol compound residue), which are of value as intermediates of antibacterial agents, are selectively produced in a high yield by bringing a diester compound of the general formula:

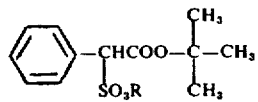

(wherein R has the same meaning as defined above) into contact with a strong acid.

7 Claims, No Drawings

PROCESS FOR PRODUCING α-SULFOPHENYLACETIC ACID DERIVATIVES

This invention relates to a method for producing α-sulfophenylacetic acid derivatives which are represented by the general formula:

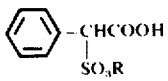   (I)

(wherein R stands for a substituted or unsubstituted primary alcohol, cyclic alcohol or phenol compound residue). Throughout the specification and claims, the alcohol residue or phenol residue means a residue which is formed by removing hydroxy group from the alcohol molecule or the phenol molecule, respectively.

Heretofore, various processes are known for the production of sulfonic acid esters. For example, the process comprising reacting silver chloronaphthalenesulfonate with ethyl iodide (Berichte Der Deutschen Chemischem Gesellschaft 25, 2482, 1892), the process comprising reacting allylsulfonyl chloride with alcohol (Journal of American Chemical Society 55, 347, 1933), the process comprising reacting aniline-o-sulfonic acid with dimethyl sulfate (Berichte Der Deutscheh Chemic Gesellschaft 53, 2346, 1920) and the process in which chlorosulfonylacetic acid with phenol (the Journal of Organic Chemistry 33, 2113, 1968) may be mentioned. However, by these processes it is impossible to accomplish a selective esterification of the sulfo group of a compound containing both a sulfo and a carboxyl group within its molecule and, if possible, the processes require complicated reaction procedures and afford only poor yields, thus being commercially unfeasible at all.

Under the circumstances we conducted an intensive research and ultimately discovered tht by permitting a strong acid to act upon a diester compound of the general formula:

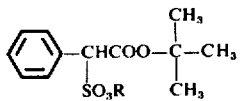   (II)

(wherein R is as previously defined) one is able to selectively cleave (de-esterify) the carboxylic tertiary butyl ester linkage alone in high yield without affecting the sulfonic ester linkage in any manner and thereby to produce an α-sulfophenylacetic acid derivative (I), and also that this diester compound (II) can be produced by reacting α-chlorosulfonylphenylacetyl chloride with tertiary butanol and further reacting the resultant α-chlorosulfonylphenylacetic acid tertiary butyl ester with a substituted or unsubstituted primary alcohol, cyclic alcohol or phenol compound. This invention is the culmination of the above surprising and unexpected findings.

Accordingly, the invention is directed to:

1. A process for producing an α-sulfophenylacetic acid derivative (I) characterized by bringing a diester compound (II) into contact with a strong acid.

2. A process for producing an α-sulfophenylacetic acid derivative (I) characterized by reacting α-chlorosulfonylphenylacetyl chloride with tertiary butanol, reacting the resultant α-chlorosulfonylphenylacetic acid tertiary butyl ester with a substituted or unsubstituted primary alcohol, cyclic alcohol or phenol compound and bringing the resultant diester compound (II) into contact with a strong acid.

According to the method of this invention, α-chlorosulfonylphenylacetyl chloride is reacted with tertiary butanol to begin with. Preferably each mole of α-chlorosulfophenylacetyl chloride is reacted with tertiary butanol. The amount of tertiary butanol relative to α-chlorosulfonylphenylacetyl chloride is not critical, but it is usually in a range from about 0.8 to 1.3 moles, more preferably 1 mole to per mole of α-chlorosulfonylphenylacetyl chloride. The reaction proceeds in the absence of a solvent, but it is preferably carried out in a solvent which does not disturb the reaction. The suitable solvent is exemplified by dichloromethane, chloroform, carbon tetrachloride, ethyl acetate, ether, tetrahydrofuran, etc. The reaction may be allowed to proceed rapidly in the presence of a conventional acid acceptor which may be an organic or inorganic base such as, for example, pyridine, α,β or γ-picoline, 2,4-lutidine, 2,6-lutidine, 3,4-lutidine, 3,5-lutidine, quinoline, isoquinoline, triethylamine, sodium hydroxide, sodium hydrogen carbonate, etc. The amount of the base is usually theoretical amount or more. Desirably the reaction is carried out within the temperature range of −30° to 30° C and, for better results, from −15° to 15°C. The reaction time ordinarily ranges from 20 minutes to 300 minutes, although these limits are not critical. The resultant α-chlorosulfonylphenylacetic acid tertiary butyl ester can be isolated by routine procedures such as concentration, crystallization, recrystallization, solvent extraction, pH adjustment, phasic transfer and chromatography before it is used as the starting material in the next reaction step. Alternatively the product can be subjected to the next reaction without prior isolation and purification.

Then, this α-chlorosulfonylphenylacetic acid tertiary butyl ester is reacted with a substituted or unsubstituted primary alcohol, cyclic alcohol or phenol compound represented by the general formula of ROH in which R has the same meaning as defined above.

The primary alcohol may be straight or branched. Thus the primary alcohol residue represented by R may be a straight primary alcohol residue, which is exemplified by methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-cosyl, n-eicosyl, n-docosyl, etc. The branched primary alkyl alcohol residue represented by R is exemplified by isobutyl, 2,2-dimethylpropyl, 2-methylbutyl, 3-methylbutyl, 2,2-dimethylbutyl, 2-methylpentyl, 2,3-dimethylbutyl, 2-ethylbutyl, 3,3-dimethylbutyl, 3-methylpentyl, 4-methylpentyl, 2,2-dimethylpentyl, 2-methylhexyl, 2,4-dimethylpentyl, 2,2,3-trimethylbutyl, 2-ethyl-3-methylbutyl, 5-methylhexyl, 2-ethyl-2-methylhexyl, 3-ethylpentyl, 2,2,4-trimethylpentyl, 2-ethyl-4-methylpentyl, 3-ethylhexyl, 2,2-dimethylhexyl, 2-(1'-methylethyl)-pentyl, 2,5-dimethylhexyl, 2,2-diethylbutyl, 6-methylheptyl, 2-(1'-methylethyl)-4-methylpentyl, 2,2-dimethylheptyl, 3,5,5-trimethylhexyl, 2,2,5-trimethylhexyl, 2-methyloctyl, 2,6-dimethylheptyl, 2-ethyl-5-methylhexyl, 2,2-diethylpentyl, 2,2-diethyl-3-methylbutyl, 7-methyloctyl, 2-butylhexyl, 2,2,6-trimethylheptyl, 8-methylnonyl, 3-ethyl-6-methylheptyl, 2,2-diethyl-4-methylpentyl, 2-methylnonyl, 2,2- diethyl-5-methylhexyl, 9-methyldecyl, 2-ethyl-6-methylnonyl, 2-methyldodecyl, 2-methyl-10-methylundecyl, 3-ethyldodecyl, 2-(1'-methylethyl)-9-methyldecyl, 2-(1'-methylethyl)-dodecyl, etc. The primary alcohols may have suitable substituents on the carbon atoms of their straight or branched chains, said substituents including, among others, halogen such as chlorine, bromine, iodine and fluorine, various acylamino groups such as acetylamino, chloroacetylamino, dichloroacetylamino, propionylamino, isobutyloylamino, etc., alkoxyl groups such as methoxy, ethoxy, propoxy, isopropoxy, butoxy, etc., aryloxy groups such as phenoxy, tolyloxy, etc., aryl groups such as phenyl, tolyl, naphthyl, etc., cyclic alkyl groups such as cyclohexyl, cyclopentyl, etc., acyloxy groups such as acetyloxy, propionyloxy, chloroacetyloxy, dichloroacetyloxy, isobutyloyloxy, etc., alkoxycarbonyl groups such as ethoxycarbonyl, methoxycarbonyl, propoxycarbonyl, etc., and heterocyclic groups such as pyridyl, pyrrolyl, furyl, thienyl, etc.

Thus examples of such substituted primary alcohol residue includes acetylaminoethyl, dichloroacetylaminopropyl, isopropyloxyethyl, 2-dichloroacetylamino-2-methylpropyl, normal-butoxyethyl, p-tert-butylphenoxyethyl, phenoxyethyl, 2-phenylethyl, 2,2-diphenylethyl, 3-phenylpropyl, 2-(N-dichloroacetyl)pyrrolidylmethyl, ethoxycarbonylmethyl, isobutyloyloxyethyl, etc.

Furthermore, it is to be noted that most important species of the primary alcohol residue R are isobutyl and a substituent represented by CH$_2$R' in which R' is a branched alkyl group of 4 to 14 carbon atoms. The symbol R' is exemplified by 1,1-dimethylethyl, 1-methylpropyl, 2-methylpropyl, 1,1-dimethylpropyl, 1-methylbutyl, 1,2-dimethylpropyl, 1-ethylpropyl, 2,2-dimethylpropyl, 2-methylbutyl, 3-methylbutyl, 1,1-dimethylbutyl, 1-methylpentyl, 1,3-dimethylbutyl, 1,1,2-trimethylpropyl, 1-ethyl-2-methylpropyl, 4-methylpentyl, 1-ethyl-1-methylpropyl, 1-ethylbutyl, 2-ethylbutyl, 1,1,3-trimethylbutyl, 1-ethyl-3-methylbutyl, 1-ethylpentyl, 2-ethylpentyl, 1,1-dimethylpentyl, 1-(1-methylethyl)-butyl, 1,4-dimethylpentyl, 1,1-diethylpropyl, 5-methylhexyl, 1-(1-methylethyl)-3-methylbutyl, 1,1-dimethylhexyl, 2,4,4-trimethylpentyl, 1,1,4-trimethylpentyl, 1-methylheptyl, 1,5-dimethylhexyl, 1-ethyl-4-methylpentyl, 1,1-diethylbutyl, 1,1-diethyl-2-methylpropyl, 6-methylheptyl, 1-butylpentyl, 1,1,5-trimethylhexyl, 7-methyloctyl, 2-ethyl-5-methylhexyl, 1,1-diethyl-3-methylbutyl, 1-methylnonyl, 8-methylnonyl, 1,1-diethyl-4-methylpentyl, 1-ethyl-5-methyloctyl, 1-methylundecyl, 1-methyl-9-methyldecyl, 2-ethylundecyl, 1-(1-methylethyl)-8-methylnonyl, 1-(1-methylethyl)-undecyl and so on.

Any kind of cyclic alcohols can be employed successfully in the method of the present invention. Such a cyclic alcohol is exemplified by cyclopropyl alcohol, cyclobutyl alcohol, cyclopentyl alcohol, cyclohexyl alcohol, cycloheptyl alcohol, cyclooctyl alcohol, cyclononyl alcohol, cyclodecyl alcohol or the like.

The cyclic alcohols may have any of the substituent groups mentioned in connection with the above primary alcohol or any of the above mentioned primary alcohol residues on their respective rings. Specific examples of such substituted cyclic alcohols include 4-chlorocyclohexanol, 2,3-dichlorocyclohexanol, 3,3,5-trimethylcyclohexanol, 4-acetylaminocyclohexanol, etc.

As said phenol compound, use is made of phenol and the compounds having from 1 to 3 substituent groups in optional positions on the penzene ring and these substituents may form a ring structure. The phenol compound may be phenol or substituted phenols. The substituents on the benzene ring may more commonly be any of the substituent groups mentioned above in connection with said primary alcohols and lower alkyl and alkenyl groups such as methyl, ethyl, propyl, isopropyl, allyl, vinyl, etc., to name but a few. The more common examples of such substituted phenol compounds include p-chlorophenol, o,p-dichlorophenol, p-methylphenol, p-methoxyphenol, dichloroacetylaminophenol, 2,6-dimethoxyphenol, 2,4,6-trimethylphenol, 5-oxyhydroinden, β-naphthol, etc.

While such a substituted or unsubstituted primary alcohol, cyclic alcohol or phenol compound can be reacted with α-chlorosulfonylphenylacetic acid tertiary butyl ester. The amount of the substituted or unsubstituted primary alcohol, cyclic alcohol or phenol compound relative to α-chlorosulfophenylacetic acid tertiary butyl ester is not critical but it is usually not less than 1 mole per mole of the latter compound. However one mole of the former compound to the latter compound is enough.

The reaction proceeds in the absence of a solvent, but it is preferably carried out in a solvent which does not disturb the reaction. For example solvents similar to those useful for the above reaction of α-chlorosulfonylphenylacetyl chloride with tertiary butanol can be employed. To allow the reaction to proceed more advantageously, it is good practice to add a base of the type mentioned above as an acid acceptor to the solvent. This reaction is desirably conducted at −20°C to 40°C and, for still better results, at −5°C to 15°C. The reaction time varies from 20 to 150 hours and, more usually from 30 to 60 minutes.

After the reaction, the resultant diester compound (II) can be used in the next reaction. Of course, the diester compound can be purified according to per se known means, for example, by washing with water to remove the acid acceptor or/and conventional isolation procedures, and optionally further by recrystallization from an organic solvent e.g. dichloromethane, chloroform, ethanol, or methanol, before the next reaction.

The diester compound (II) thus obtained is then brought into contact with a strong acid. The strong acid to be used in the reaction may be any acid that will not interfer with (i.e. will not deesterfy) a sulfonic ester linkage of diester(II) and that is able to convert a carboxylic acid tertiary ester to a carboxyl acid. The strong acid is exemplified by a strong inorganic acid such as mineral acid e.g. sulfuric acid, hydrochloric acid, hydrobromic acid, etc.; a strong organic sulfonic acid such as an aryl sulfonic acid e.g. phthalsulfonic acid, benzenesulfonic acid, toluenesulfonic acid etc.; and a strongly acidic iron exchange resins e.g. Amberlite 200, Amberlyst 15, etc.

While these acids, used in very small amounts, i.e. catalytic amounts, attain the purposes of the reaction,, they may optionally be used in far excess. However, 0.01 to 3 moles of each of these acids per 1 mole of the diester compound (II) is usual amount.

The reaction proceeds in the absence of a solvent, but it is preferably conducted in a solvent. Any solvent which does not disturb the reaction is employable. Suitable solvents may for example be dichloromethane, chloroform, carbon tetrachloride, benzene or toluene, to name but a few of the common solvents.

The reaction temperature is usually from −30°C to 50°C and, preferably −20°C to 20°C.

While the reaction is ordinarily carried out over a period of 20 minutes to 3 days, it may be continued for longer than 3 days. Generally speaking, when the acid used is inorganic or organic one, the reaction goes to conclusion in a short time. Conversely, when the ion exchange resin is used, the reaction is desirably conducted for a relatively long time. The end of the reaction can be confirmed by per se known means for example thin layer chromatography. After the reaction has been completed, the product α-sulfophenylacetic acid derivative (I) can be isolated by such known procedures as concentration, crystallization, recrystallization, solvent extraction, phasic transfer and chromatography. The product (I) may be purified and separated by conventional means. For example, the desired compound (I) can be obtained in higher purity by the steps of adding sodium hydroxide, potassium hydroxide or the like to the reaction product to obtain an aqueous solution of the sodium or potassium salt of (I), neutralizing the solution with a suitable acid, extracting the product with an organic solvent e.g. dichloromethane, chloroform, benzene, ethyl acetate or the like, removing the solvent by distillation, dissolving the residue in a solvent such as chloroform, dichloroethane, carbon tetrachloride, etc. and carrying out a chromatographic separation on silica gel, alumina or the like. Alternatively, the desired compound can also be obtained in a very high purity by adding benzene, n-hexane, petroleum ether or the like to a solution of compound (I) in chloroform, dichloromethane or the like and stirring and, then, cooling the solution to let compound (I) separate out as crystals.

In the α-sulfophenylacetic acid derivatives (I) of the present invention, the α-carbon atom constitutes an asymmetric carbon atom and there exists at least two optical isomers. It is to be understood tat all such isomeric forms as well as mixtures thereof are included in the scope of the present invention. When the reaction product is obtained as a mixture of isomers, if desired the mixture may be resolved optically into the respective isomers, for example by chromatography or recrystallization of their salts with optically active bases, according to per se known procedures. Alternatively, the optically active α-sulfophenyl acetic acid derivatives (I) are produced by employing an optically active diester compound of the general formula (II) or an optically active α-chlorosulfonylphenylacetyl chloride.

The α-sulfophenylacetic acid derivative (I) itself or its reactive derivative (e.g. corresponding acid chloride) which is prepared from α-sulfophenylacetic acid derivative (I) according to per se known means is reacted with 6-aminopenicillanic acid or its silyl derivative according to per se known means and, in case where the silyl derivative is employed, the silyl group is removed through hydrolysis or alcoholysis according to per se known means to obtain corresponding penicillins of the general formula:

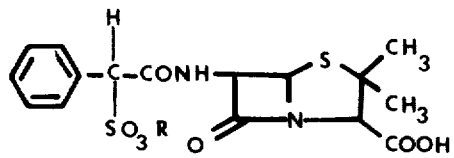

or their salts. Those penicillins are effective against gram-positive bacteria as well as gram-negative bacteria, especially *Pseudomonas aeruginosa* and can effectively be administered orally.

When one of those penicillin compounds is orally administered, it is readily absorbed into the body from the intestinal tract to give α-sulfobenzylpenicillin in vibo and to attain a high blood concentration as α-sulfobenzylpenicillin, thereby acting as potent antibiotics upon such microorganisms as gram-positive bacteria, gram-negative bacteria, *Pseudomonas aeruginosa* and penicillin G-resistant bacteria. Those penicillins are also characterized by that those are stable during storage and have excellent shelf-lives when stored in the atmosphere.

From the view point of using the compounds (I) as the starting materials for the production of those penicillins, the most important residue R in the above general formulas are isobutyl and —$CH_2R'$ is a branched alkyl of 4 to 14 carbon atoms.

Those penicillin compounds or their pharmaceutically acceptable salts can be administered, either as such or after compounding it with pharmaceutical excipients or carriers, in such dosage forms as powders, granules, tablets, capsules, suppositories, injections and so on. The recommended unit dosage amount for an adult human is 0.1 to 1 gram in terms of amount of α-sulfobenzylpenicillin. The unit dosage is administered every 1 to several hours.

EXAMPLE 1

1. In 100 ml. of dichloromethane is dissolved 25.5 g. of α-chlorosulfonylphenylacetyl chloride, and after the solution is cooled to −10°C, a mixture of 7.9 g. of pyridine and 7.4 g. of tertiary butanol is added dropwise at the same temperature. After the dropwise addition has been completed, the reaction mixture is brought to 0°C, at which temperature it is reacted under stirring for 30 minutes. To the reaction mixture is added 100 ml. of ethyl acetate, followed by cooling. The precipitated pyridine hydrochloride is removed by suction filtration and the filtrate is concentrated to dryness. The procedure yields 27.2 g. of pale yellowish white crystalline powders of α-chlorosulfonylphenylacetic acid tertiary butyl ester, melting at 56°–57°C.
NMR($CDCl_3$), δ ppm: 1.53($s$, 9H), 5.44($s$, 1H), 7.50($m$, 5H); IR(KBr, $cm^{-1}$): 1738, 1375, 1170, 1134.

2. In 120 ml. of dichloromethane are dissolved 27 g. of the powders of α-chlorosulfonylphenylacetic acid tertiary butyl ester obtained in (1). The solution is cooled to 0°C and a mixture of 7.5 g. of pyridine and 14.9 g. of n-decyl alcohol is added dropwise at the same temperature. After the dropwise addition has been completed, the reaction mixture is brought to 25°C at which temperature it is stirred for 30 minutes. The precipitated pyridine hydrochloride is removed by suction filtration and the filtrate is washed twice with 40 ml. portions of water, dried over 20 g. of sodium sulfate and finally concentrated to dryness. The procedure yields 35.1 g. of pale yellowish powders of α-n-decylsulfophenylacetic acid tertiary butyl ester melting at 52°–53°C.
IR(KBr, $cm^{-1}$): 2950, 1733, 1370, 1138, 927; NMR($CDCl_3$, δ ppm): 0.84($m$, 3H), 1.00–1.75(broad $s$, 16H), 1.42($s$, 9H), 4.00($t$, 2H), 5.00($s$, 1H), 7.30–7.70(broad $m$, 5H).

3. In 120 ml. of dichloromethane is dissolved 35 g. of the α-n-decylsulfophenylacetic acid tertiary butyl ester prepared according to (2) above. The solution is cooled to 0°C and 12.9 g. of concentrated sulfuric acid is added. The mixture is reacted under stirring at the same temperature for 30 minutes, after which time 60 ml. of dichloromethane is further added. The mixture is washed twice with 60 ml. portions of water and, then, 60 ml. of cold water is added. The mixture is adjusted to pH 6.8 with 1N sodium hydroxide and the water layer is separated, followed by the addition of 180 ml. of dichloromethane. The mixture is adjusted to pH 2.0 with 1N hydrochloric acid and the dichloromethane layer is dried over sodium sulfate and concentrated to dryness. The procedure yield 28.7 g. of colorless crystals of α-n-decylsulfophenylacetic acid.

In the above method (3), hydrobromic acid is used in the place of sulfuric acid to obtain the same product.

EXAMPLE 2

In 40 ml. of dichloromethane is dissolved 9.7 g. of α-2,2,4-trimethylpentylsulfophenylacetic acid tertiary butyl ester and, after the solution is cooled at 0°C, 2.94 g. of 90 % sulfuric acid is added. The mixture is reacted under stirring at the same temperature for 3 hours. After the reaction, 150 ml. of diethyl ether is added to the reaction mixture, which is then washed twice with 30 ml. portions of cold water. After the addition of 30 ml. of water, the pH is brought to 6.8 with 1N sodium hydroxide. The water layer is separated and 120 ml. of ethyl acetate is added. The mixture is adjusted to pH 2.0 with 1N hydrochloric acid and the ethyl acetate layer is further washed twice with 40 ml. portions of water and concentrated to dryness. To the concentrate is added 200 ml. of n-hexane and the mixture is stirred at 0°C for 60 minutes, whereupon colorless crystals are produced. These crystals are collected by filtration, washed with 40 ml. of n-hexane and dried under reduced pressure and at 40°C for 6 hours. The procedure yields 5.9 g. of colorless crystals of α-2,2,4-trimethylpentylsulfophenylacetic acid, melting at 95°–96°C.

EXAMPLE 3

In 10 ml. of dichloromethane is dissolved 40 g. of α-cyclohexylsulfophenylacetic acid tertiary butyl ester. After cooling with ice, 5 ml. of a 30 % solution of hydrogen bromide in acetic acid is added. The mixture is stirred to react at the same temperature for 60 minutes, after which 100 ml. of cold water is added. The reaction mixture is extracted twice with 100 ml. portions of chloroform and the chloroform layer is washed with 50 ml. of water, followed by the addition of 50 ml. of water. The mixture is adjusted to pH 6.9 with 1N sodium hydroxide and the water layer is taken, followed by the addition of 100 ml. of chloroform. The pH is brought to 2.2 with 1N hydrochloric acid and the chloroform layer is taken and washed with 50 ml. of water. The chloroform layer is taken, dried over 10 g. of magnesium sulfate and concentrated to dryness. The procedure yields 2.8 g. pale yellowish white crystals of α-cyclohexylsulfophenylacetic acid melting at 69°–71°C.

EXAMPLE 4

In 80 ml. of benzene is dissolved 17.5 g. of α-phenylsulfophenylacetic acid tertiary butyl ester. The solution is cooled to 10°C and 19.4 g. of dry p-toluenesulfonic acid is added. The mixture is stirred to react at the same temperature for 5 hours, after which it is washed twice with 30 ml. portions of cold water. Following the addition of 75 ml. of water, the pH is adjusted to 6.8 with 1N sodium hydroxide and the water layer is taken. Then, 150 ml. of ethyl acetate is added and the pH is brought to 2.0 with 1N hydrochloric acid. The ethyl acetate layer is taken, washed twice with 75 ml. of water and concentrated to dryness. The described procedure yields 12.8 g. colorless crystals of α-phenylsulfophenylacetic acid melting at 106°–107°C.

In the above method, phthalsulfonic acid or benzenesulfonic acid is used in the place of p-toluenesulfonic acid to obtain the same product.

EXAMPLE 5

In 20 ml. of dichloromethane is dissolved 4.2 g. of α-2,2,2-trichloroethylsulfophenylacetic acid tertiary butyl ester, followed by the addition of 28 g. of Amberlite 200 (strongly acidic iron exchange resin, H-form, dried product). The mixture is stirred to react at 25°C for 3 days. After the reaction, the Amberlite 200 is removed by suction filtration and the filtrate is washed twice with 10 ml. of water. Following the addition of 20 ml. of water, the pH is brought to 6.8 with 1N sodium hydroxide and the water layer is taken. To this layer is added 40 ml. of ethyl acetate and the pH is brought to 2.2 with 1N hydrochloric acid. The ethyl acetate layer is washed twice with 20 ml. portions of water and concentrated to dryness. The described procedure yields 4.1 g. colorless crystals of α-2,2,2-trichloroethylsulfophenylacetic acid melting at 122°–123°C. In the above method, Amberlyst 15 is used in the place of Amberlite 200 to obtain the same product.

The following table gives a partial listing of the contemplated product α-sulfophenylacetic acid derivatives of the general formula:

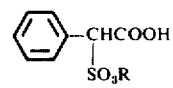

and the physicochemical constants (IR and NMR) of these derivatives, said derivatives having been produced by reacting the α-chlorosulfophenylacetic acid tertiary butyl ester according to Example 1 (1) with various primary alcohols, cyclic alcohols or phenol compounds in the manner described in Example 1 (2) to obtain α-sulfophenylacetic acid diesters of the general formula:

and, then, cleaving the respective carboxylic tertiary butyl esters with acid in one of the manners set forth in Example 1-(3) and Examples 2, 3, 4 and 5.

Methods of acid cleavage of compounds and their physicochemical constants

| Substituent group R | No. of corresponding Example | Infrared absorption spectrum KBr, cm$^{-1}$ | Nuclear magnetic resonance spectrum (CDCl$_3$)δ ppm |
|---|---|---|---|
| —CH$_3$ | 1 - (3) | 1710,1365, 1175 | 7.55(5H),5.25(1H), 3.84(3H) |
| —CH$_2$CH$_3$ | 1 - (3) | 1710,1360, 1174 | 7.45(5H),5.17(1H), 4.17(2H),1.26(3H) |
| —CH$_2$CH$_2$CH$_3$ | 1 - (3) | 1710,1355, 1170 | 7.25-7.70(5H),5.12 (1H),4.06(2H),1.35- 1.9(2H),0.88(3H) |
| —CH$_2$(CH$_2$)$_2$CH$_3$ | 1 - (3) | 1712,1365, 1170 | 7.44(5H),5.20(1H), 4.10(2H),1.00- 1.80(4H),0.84(3H) |
| —CH$_2$CH(CH$_3$)$_2$ | 2 | 1710,1365, 1170 | 7.30-7.70(5H), 5.24(1H),3.90(2H), 1.60-2.25(1H), 0.96(6H) |
| —CH$_2$(CH$_2$)$_4$CH$_3$ | 1 - (3) | 1715,1360, 1170 | 7.30-7.80(5H), 5.25(1H),4.15(2H), 1.10-2.00(8H), 0.95(3H) |
| —CH$_2$(CH$_2$)$_5$CH$_3$ | 1 - (3) | 1710,1360, 1165 | 7.30-7.75(5H), 5.20(1H),4.12(2H), 1.05-1.85(8H), 0.85(3H) |
| —CH$_2$(CH$_2$)$_6$CH$_3$ | 1 - (3) | 1710,1365, 1172 | 7.27-7.77(5H), 5.20(1H),4.10(2H), 1.05-1.87(12H), 0.89(3H) |
| —CH$_2$(CH$_2$)$_8$CH$_3$ | 1 - (3) | 1710,1365, 1170 | 7.30-7.70(5H), 5.18(1H),4.10(2H), 1.05-1.80(16H), 0.87(3H) |
| —CH$_2$(CH$_2$)$_{10}$CH$_3$ | 1 - (3) | 1712,1365, 1170 | 7.30-7.70(5H), 5.15(1H),4.10(2H), 1.10-1.80(20H), 0.86(3H) |
| —CH$_2$(CH$_2$)$_{12}$CH$_3$ | 1 - (3) | 1712,1360, 1168 | 7.31-7.71(5H), 5.19(1H),4.09(2H), 1.06-1.86(24H), 0.88(3H) |
| —CH$_2$(CH$_2$)$_{14}$CH$_3$ | 1 - (3) | 1710,1360, 1168 | 7.21-7.71(5H), 5.08(1H),4.08(2H), 1.08-1.81(28H), 0.86(3H) |
| —CH$_2$(CH$_2$)$_{16}$CH$_3$ | 1 - (3) | 1712,1363, 1170 | 7.35-7.80(5H), 5.20(1H),4.12(2H), 1.05-1.80(32H), 0.90(3H) |
| —CH$_2$(CH$_2$)$_{18}$CH$_3$ | 1 - (3) | 1712,1363, 1170 | 7.30-7.60(5H), 5.18(1H),4.12(2H), 1.10-1.70(36H), 0.90(3H) |
| —CH$_2$(CH$_2$)$_{20}$CH$_3$ | 1 - (3) | 1715,1365, 1170 | 7.25-7.80(5H), 5.13(1H),4.09(2H), 1.05-1.90(40H), 0.89(3H) |
| —CH$_2$—C(CH$_3$)$_3$ | 2 | 1715,1370, 1175 | 7.10-7.70(5H), 5.10(1H),3.70(2H), 0.80(9H) |
| —CH$_2$CH(CH$_3$)CH$_2$CH$_3$ | 3 | 1710,1360, 1170 | 7.20-7.60(5H), 5.19(1H),3.96(2H), 1.05-1.90(3H), 0.86(6H) |
| —CH$_2$CH$_2$CH(CH$_3$)$_2$ | 1 - (3) | 1715,1370, 1170 | 7.20-7.65(5H), 5.16(1H),4.16(2H), 1.25-1.95(3H), 0.85(6H) |
| —CH$_2$—C(CH$_3$)$_2$—CH$_2$—CH$_3$ | 5 | 1720,1360, 1170 | 7.20-7.70(5H), 5.16(1H),3.75(2H), 1.10(2H),0.82(5H) |
| —CH$_2$—CH(CH$_3$)—CH(CH$_3$)$_2$ | 1 - (3) | 1715,1365, 1172 | 7.20-7.65(5H), 5.20(1H),3.95(2H), 1.05-1.60(5H), 0.86-0.91(3H) |
| —CH$_2$—CHCH(CH$_3$)$_2$ with CH$_3$ | 1 - (3) | 1735,1365, 1170 | 7.30-7.70(5H), 5.20(1H),3.99(2H), 1.30-1.90(2H), 0.80-0.86(9H) |
| —CH$_2$CH(CH$_2$CH$_3$)CH$_2$CH$_3$ | 1 - (3) | 1720,1370, 1172* | 7.30-7.70(5H), 5.20(1H),4.06(2H), 1.0-1.70(5H), 0.81(6H) |

-continued

| Methods of acid cleavage of compounds and their physicochemical constants | | | |
|---|---|---|---|
| Substituent group R | No. of corresponding Example | Infrared absorption spectrum KBr, cm$^{-1}$ | Nuclear magnetic resonance spectrum (CDCl$_3$)δ ppm |
| $-CH_2-CH_2-C(CH_3)_3$ | 1 - (3) | 1712, 1365, 1170 | 7.25–7.70(5H), 5.12(1H), 4.15(2H), 1.55(2H), 0.86(9H) |
| $-CH_2CH_2CH(CH_3)CH_2CH_3$ | 1 - (3) | 1715, 1360, 1170 | 7.30–7.70(5H), 5.18(1H), 4.10(2H), 1.02–1.68(5H), 0.92(3H), 0.86(3H) |
| $-CH_2CH_2CH_2CH(CH_3)_2$ | 1 - (3) | 1715, 1370, 1170 | 7.30–7.70(5H), 5.19(1H), 4.12(2H), 1.00–1.85(5H), 0.86(6H) |
| $-CH_2-C(CH_3)_2-(CH_2)_2-CH_3$ | 5 | 1735, 1360, 1172* | 7.25–7.70(5H), 5.22(1H), 3.81(2H), 1.05–1.68(4H), 0.90(3H), 0.86(6H) |
| $-CH_2CH(CH_3)(CH_2)_3-CH_3$ | 5 | 1716, 1360, 1170 | 7.35–7.85(5H), 5.25(1H), 3.95(2H), 1.05–2.00(7H), 0.91(6H) |
| $-CH_2CH(CH_3)CH_2CH(CH_3)_2$ | 1 - (3) | 1720, 1368, 1172 | 7.28–7.68(5H), 5.20(1H), 3.96(2H), 1.08–1.90(4H), 0.92(3H), 0.88(6H) |
| $-CH_2-C(CH_3)_2-CH(CH_3)_2$ | 5 | 1720, 1364, 1172 | 7.30–7.70(5H), 5.21(1H), 3.85(2H), 1.10–1.75(1H), 0.84–0.90(12H) |
| $-CH_2CH(CH_3)_2$ (as $-CH_2CHCH(CH_3)_2$ with CH$_3$) | 1 - (3) | 1715, 1362, 1170 | 7.30–7.75(5H), 5.20(1H), 4.03(2H), 1.08–1.82(2H), 0.89(3H), 0.86(6H) |
| $-CH_2CH(CH_2CH_3)CH_2CH_2-CH_3$ | 1 - (3) | 1716, 1365, 1173 | 7.30–7.70(5H), 5.20(1H), 4.03(2H), 1.10–1.90(5H), 0.85–0.90(6H) |
| $-CH_2(CH_2)_3CH(CH_3)_2$ | 1 - (3) | 1715, 1368, 1170 | 7.30–7.65(5H), 5.18(1H), 4.14(2H), 1.05–1.75(7H), 0.86(6H) |
| $-CH_2-C(CH_3)(CH_2CH_3)-CH_2-CH_3$ | 1 - (3) | 1715, 1365, 1172 | 7.30–7.70(5H), 5.20(1H), 3.98(2H), 1.17–1.95(4H), 0.86–0.91(9H) |
| $-CH_2-C(CH_3)_2-CH_2CH(CH_3)_2$ | 2 | 1724, 1362, 1173 | 7.30–7.70(5H), 5.20(1H), 3.80(2H), 1.10–1.70(3H), 0.85–0.90(12H) |
| $-CH_2CH(CH_2CH_3)CH_2CH(CH_3)_2$ | 1 - (3) | 1714, 1368, 1170 | 7.30–7.70(5H), 5.20(1H), 4.03(2H), 1.00–1.80(4H), 0.82–0.86(9H) |
| $-CH_2CH(CH_2CH_3)(CH_2)_3-CH_3$ | 1 - (3) | 1712, 1360, 1170 | 7.30–7.75(5H), 5.16(1H), 4.05(2H), 1.00–1.65(9H), 0.91(3H), 0.85(3H) |
| $-CH_2(CH_2)_4CH(CH_3)_2$ | 1 - (3) | 1715, 1365, 1172 | 7.30–7.65(5H), 5.19(1H), 4.09(2H), 1.05–1.82(9H), 0.85(6H) |
| $-CH_2-C(CH_3)_2-(CH_2)_3-CH_3$ | 2 | 1720, 1362, 1173 | 7.30–7.70(5H), 5.20(1H), 3.80(2H), 1.10–1.90(8H), 0.88(3H), 0.85(6H) |
| $-CH_2CH(CH_3)(CH_2)_2-CH_3$ with $-CH(CH_3)_2$ | 1 - (3) | 1728, 1368, 1170 | 7.30–7.70(5H), 5.20(1H), 3.98(2H), 1.10–1.75(6H), 0.89(3H), 0.85(6H) |
| $-CH_2CH(CH_3)(CH_2)_2CH(CH_3)_2$ | 1 - (3) | 1720, 1360, 1170 | 7.30–7.70(5H), 5.21(1H), 3.95(2H), 1.00–1.90(6H), 0.84–0.88(9H) |
| $-CH_2C(CH_2CH_3)_3$ | 1 - (3) | 1722, 1360, 1168 | 7.30–7.70(5H), 5.16(1H), 3.83(2H), 1.05–1.70(6H), 0.82–0.90(9H) |
| $-CH_2-CH_2-CH(CH_3)-CH_2-C(CH_3)_3$ | 1 - (3) | 1720, 1370, 1170 | 7.30–7.70(5H), 5.18(1H), 4.15(2H), 1.08–2.70(5H), 0.84–0.88(12H) |

-continued

| | Methods of acid cleavage of compounds and their physicochemical constants | | |
|---|---|---|---|
| Substituent group R | No. of corresponding Example | Infrared absorption spectrum KBr, cm$^{-1}$ | Nuclear magnetic resonance spectrum (CDCl$_3$)δ ppm |
| —CH$_2$C(CH$_3$)—(CH$_2$)$_2$CH(CH$_3$)$_2$ with CH$_3$ | 5 | 1721,1365, 1172 | 7.25–7.65(5H), 5.18(1H),3.82(2H), 1.10–1.75(5H), 0.85–0.88(12H) |
| —CH$_2$CH(CH$_2$CH(CH$_3$)$_2$)CH(CH$_3$)$_2$ | 1 - (3) | 1725,1368, 1172 | 7.30–7.70(5H), 5.20(2H),3.98(2H), 1.00–1.65(4H), 0.86–0.90(12H) |
| —CH$_2$—C(CH$_3$)$_2$—(CH$_2$)$_4$—CH$_3$ | 2 | 1730,1362, 1170 | 7.30–7.70(5H), 5.20(1H),3.80(2H), 1.12–1.95(8H), 0.89(3H),0.85(6H) |
| —CH$_2$CH((CH$_2$)$_3$CH$_3$)(CH$_2$)$_3$CH$_3$ | 1 - (3) | 1715,1360, 1172 | 7.40–7.75(5H), 5.25(1H),4.08(2H), 1.30–1.90(13H), 0.9(6H) |
| —CH$_2$—C(CH$_3$)$_2$(CH$_2$)$_3$CH(CH$_3$)$_2$ | 2 | 1726,1368, 1172 | 7.35–7.70(5H), 5.22(1H),3.84(2H), 0.95–1.76(7H), 0.84–0.89(12H) |
| —CH$_2$(CH$_2$)$_6$CH(CH$_3$)$_2$ | 1 - (3) | 1718,1370, 1170 | 7.30–7.75(5H), 5.18(1H),4.12(2H), 1.12–1.90(13H), 0.86(6H) |
| —CH$_2$CH(CH$_2$CH$_3$)(CH$_2$)$_3$CH(CH$_3$)$_2$ | 1 - (3) | 1720,1368, 1170 | 7.30–7.70(5H), 5.21(1H),4.00(2H), 1.05–1.88(10H), 0.82–0.88(9H) |
| —CH$_2$—C(CH$_2$CH$_3$)(CH$_2$CH(CH$_3$)$_2$) | 2 | 1726,1368, 1172 | 7.25–7.70(5H), 5.20(1H),3.88(2H), 0.90–1.90(7H), 0.82–0.90(12H) |
| —CH$_2$CH(CH$_3$)—(CH$_2$)$_7$CH$_3$ | 1 - (3) | 1730,1370,* 1172 | 7.30–7.70(5H), 5.22(1H),3.90(2H), 1.05–1.70(15H), 0.86–0.93(6H) |
| —CH$_2$(CH$_2$)$_7$CH(CH$_3$)$_2$ | 1 - (3) | 1732,1370,* 1172 | 7.30–7.70(5H), 5.20(1H),4.08(2H), 1.10–1.75(15H), 0.85–0.88(6H) |
| —CH$_2$—C(CH$_2$CH$_3$)$_2$(CH$_2$)$_2$CH(CH$_3$)$_2$ | 1 - (3) | 1740,1369,* 1170 | 7.30–7.70(5H), 5.20(1H),3.83(2H), 1.00–1.95(9H), 0.82–0.88(12H) |
| —CH$_2$CH(CH$_2$CH$_3$)(CH$_2$)$_3$CH(CH$_3$)$_2$ | 1 - (3) | 1735,1370,* 1171 | 7.30–7.70(5H), 5.22(1H),4.03(2H), 1.10–1.65(10H), 0.86–0.92(9H) |
| —CH$_2$CH(CH$_3$)(CH$_2$)$_9$CH$_3$ | 1 - (3) | 1750,1374,* 1172 | 7.30–7.75(5H), 5.21(1H),3.95(2H), 1.10–1.65(19H), 0.84–0.90(6H) |
| —CH$_2$CH(CH$_2$CH$_3$)(CH$_2$)$_9$CH$_3$ | 1 - (3) | 1745,1370,* 1170 | 7.30–7.70(5H), 5.20(1H),4.03(2H), 1.05–1.50(21H), 0.7–1.05(6H) |
| —CH$_2$CH(CH$_2$CH$_3$)(CH$_2$)$_7$CH(CH$_3$)$_2$ | 1 - (3) | 1745,1370,* 1168 | 7.30–7.70(5H), 5.20(1H),4.03(2H), 1.00–1.80(18H), 0.80–0.92(9H) |
| —CH$_2$CH((CH$_2$)$_6$CH(CH$_3$)$_2$)CH(CH$_3$)$_2$ | 1 - (3) | 1745,1372,* 1172 | 7.30–7.70(5H), 5.20(1H),4.00(2H), 0.93–1.70(14H), 0.82–0.92(12H) |
| —CH$_2$CH((CH$_2$)$_9$CH$_3$)CH(CH$_3$)$_2$ | 1 - (3) | 1740,1370,* 1170 | 7.25–7.70(5H), 5.22(1H),4.09(2H), 1.10–1.75(20H), 0.82–0.88(9H) |
| —CH$_2$CH((CH$_2$)$_7$CH$_3$)CH(CH$_3$)$_2$ | 1 - (3) | 1714,1368, 1170 | 7.25–7.70(5H), 5.21(1H),4.09(2H), 1.30–1.80(16H), 0.82–0.90(9H) |
| —CH$_2$—CH((CH$_2$)$_3$CH$_3$)CH(CH$_3$)$_2$ | 1 - (3) | 1730,1365, 1176 | 7.25–7.70(5H), 5.20(1H),4.15(2H), 1.30–1.90(8H), 0.82–0.88(9H) |

-continued

Methods of acid cleavage of compounds and their physicochemical constants

| Substituent group R | No. of corresponding Example | Infrared absorption spectrum KBr, cm$^{-1}$ | Nuclear magnetic resonance spectrum (CDCl$_3$)δ ppm |
|---|---|---|---|
| —CH$_2$COOC$_2$H$_5$ | 3 | 1753,1705, 1365,1168* | 7.30–7.75(5H), 5.60(1H),4.66(2H), 4.19(2H),1.23(3H) |
|  | 3 | 1745,1715, 1360,1170* | 7.25–7.70(5H), 5.25(1H),4.14(2H), 2.08(3H),1.1(6H) |
| 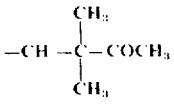 | 3 | 1750,1650–1670,1370, 1170 | 7.15–7.70(5H), 6.15(1H),4.05–4.50 (3H),3.30–3.70(2H), 1.50–2.30(2H) |
|  | 4 | 1755,1672, 1355–1330, 1135 | 7.25–7.60(5H), 6.06(1H),5.20(1H), 4.25(2H),1.25(6H) |
| 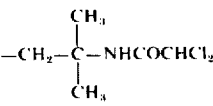 | 4 | 1730,1365, 1155 | 7.25–7.75(5H), 5.50(1H),4.11(2H), 3.60–3.90(3H), 1.40–2.20(4H) |
|  | 1 – (3) | 1733,1370, 1260,992 | 7.25–7.70(5H), 5.45(1H),4.30(2H), 3.40–3.70(4H), 1.20–1.75(4H), 0.80–1.10(3H) |
| 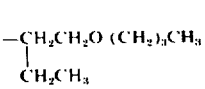 | 1 – (3) | 1495,1365, 1170 | 6.90–7.60(15H), 5.24(1H),4.50–4.80(2H),4.05–4.50(1H) |
| 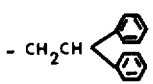 | 1 – (3) | 1720,1500, 1363,1173 | 6.90–7.65(10H), 5.10(1H),4.17(2H), 2.79(2H) |
| 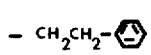 | 1 – (3) | 1720,1363, 1170 | 6.90–7.75(10H), 5.15(1H),4.05(2H), 2.55(2H),1.60–2.15(2H) |
| 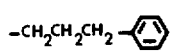 | 1 – (3) | 1720,1375, 1170 | 6.80–7.70(10H), 5.32(1H),4.05(2H), 4.42(2H),1.30(9H) |
| 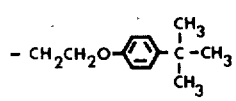 | 3 | 1710,1360, 1170 | 7.30–7.70(5H), 5.20(1H),3.44(2H), 0.85–1.85(11H) |
|  | 3 | 1715,1370, 1170 | 7.30–7.80(5H), 5.20(1H),4.70(1H), 1.10–2.10(10H) |
|  | 4 | 1705,1360, 1185,1140 | 7.00–7.90(10H), 5.50(1H) |
|  | 4 | 1715,1365, 1170 | 6.70–7.90(8H), 5.50(1H),2.90(4H), 2.15(2H) |
| —CH$_2$CH$_2$—Cl | 1 – (3) | 1720,1365, 1170 | 7.25–7.70(5H), 5.20(1H),4.20(2H), 3.85(2H) |
|  | 3 | 1750,1715, 1360,1170 | 7.22–7.70(5H), 5.24(1H),4.25(4H), 2.05(3H) |
| —CH$_2$CCl$_3$ | 1 – (3) | 1720,1382, 1181 | 7.30–7.57(5H), 5.39(1H),4.53(2H) |
| —CH$_2$CHCl$_2$ | 1 – (3) | 1720,1378, 1179 | |
| 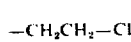 | 1 – (3) | 1710,1360, 1170 | 6.80–7.65(9H), 5.45(1H) |
| 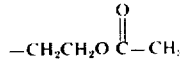 | 1 – (3) | 1715,1365–1170 | 7.00–7.70(9H), 5.50(1H),2.20(3H) |
| 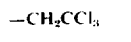 | 1 – (3) | 1710,1360, 1175 | 6.75–7.65(9H), 5.50(1H),3.80(3H) |

-continued

Methods of acid cleavage of compounds and their physicochemical constants

| Substituent group R | No. of corresponding Example | Infrared absorption spectrum KBr, cm⁻¹ | Nuclear magnetic resonance spectrum (CDCl₃)δ ppm |
|---|---|---|---|
| ⟨◯⟩-NHCOCH₂Cl₂ | 1 - (3) | 1710,1670, 1360,1175 | 6.80–7.75(9H), 6.15(1H) |
| ⟨H⟩-C(CH₃)(CH₃)CH₃ | 1 - (3) | 1715,1365,* 1170 | 7.30–7.80(5H), 5.21(1H),4.72(1H), 1.05–2.10(7H), 0.90(9H) |
| –CH₂CH₂O CH(CH₃)(CH₃) | 1 - (3) | 1717,1360, 1169 | 7.30–7.70(5H), 5.35(1H),4.30(2H), 3.42–3.68(3H), 1.10(3H),1.20(3H) |

The symbol * denotes that the sample was analyzed in the liquid form.

REFERENCE EXAMPLE 1

Production of α-2-methylpropylsulfobenzylpenicillin sodium salt

In 16 ml. of dry ether is dissolved 2.72 g. of α-2-methylpropylsulfophenylacetic acid and, then, 0.94 ml. of thionyl chloride and 0.04 ml. of N,N-dimethylformamide are added. The mixture is refluxed for 5 hours. After the reaction, the mixture is concentrated under reduced pressure to remove the unreacted thionyl chloride.

In 6 ml. of dry chloroform is suspended 2.16 g. of 6-aminopenicillanic acid, followed by the addition of 3 ml. of hexamethyldisilazane. The mixture is refluxed under stirring for 1 hour. After the reaction, the mixture is concentrated under reduced pressure at an external temperature of 50°C, whereupon a syrupy residue is obtained.

This syrupy product is dissolved in 120 ml. of dichloromethane and, while the solution is cooled to −40°C, 1.30 ml. of quinoline is added. The acid chloride previously obtained is dissolved in 40 ml. of dichloromethane and added dropwise over a period of 10 minutes. The reaction is further allowed to proceed under cooling with ice for 1 hour. Then, 120 ml. of cold ether, 80 ml. of cold water and 200 ml. of cold ether are added in that order. Then, the mixture is adjusted to pH 2.0 by the addition of 10 % hydrochloric acid. The water layer is discarded and, after washing with 80 ml. of cold water, 60 ml. of water is added and 9.2 ml. of 1N sodium hydroxide is gradually added. The water layer is recovered and, after the solvent is removed, lyophilized. The procedure yields 4.3 grams of the desired compound.

IR(KBr, cm⁻¹): 3350, 2975, 1770, 1690, 1612, 1520, 1360, 1166, 935, 692; NMR(60MHz, ppm., d₆DMSO): 0.80(3H, s.), 0.91(3H s.), 1.50(6H, t.), 1.90(1H, mult.), 3.90(1H, s.), 3.95(2H, d.), 5.40(2H, d.), 5.90(1H, s.), 7.42(5H), 9.15(1H, broad).

REFERENCE EXAMPLE 2

A carboxylic acid of general formula (I) (0.01 mole) is dissolved in 16 ml. of dry ether and 0.94 ml. of thionyl chloride and a small amount of N,N-dimethylformamide are added.

The mixture is refluxed for 5 hours. After the reaction has been completed, the reaction mixture is concentrated under reduced pressure to remove as much unreacted thionyl chloride as possible.

In 6 ml. of dry chloroform is suspended 2.16 g. (0.01 mole) of 6-aminopenicillanic acid, followed by the addition of 3 ml. of hexamethyldisilazane. The mixture is refluxed under stirring for 1 hour. After the reaction, the reaction mixture is concentrated under reduced pressure and at an external temperature of 50°C, whereupon a syrupy residue is obtained. This syrupy product is dissolved in 120 ml. of dichloromethane and the solution is cooled to −40°C. Then, 1.30 ml. of quinoline is added.

The acid chloride obtained above is dissolved in 40 ml. of dichloromethane and the solution is added dropwise over a period of 10 minutes. The mixture is further reacted under cooling with ice for 1 hour. Then, 120 ml. of cold ether, 80 ml. of cold water and 200 ml. of cold ether are added in the order mentioned. Then, the mixture is brought to pH 2.0 with 10 % hydrochloric acid. The water layer is discarded and, after washing with 80 ml. of cold water, 60 ml. of water is added. Then, the mixture is adjusted to pH 7.5 by the gradual addition of 1N sodium hydroxide. The water layer is harvested and, after the solvent is removed, lyophilized. The procedure yields the sodium salt of penicillin of general formula, mentioned below, as white to pale yellowish powders.

The infrared absorption and nuclear magnetic spectra of penicillin compounds

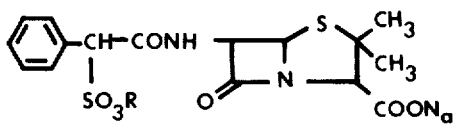

| Compound No. | Branched alkyl R | Infrared absorption spectrum (KBr, cm$^{-1}$) | Nuclear magnetic resonance spectrum (60MHz,ppm.,d$_6$DMSO) |
|---|---|---|---|
| 1 | —CH$_2$—CHCH$_2$CH$_3$<br>\|<br>CH$_2$—CH$_3$ | 3350,2970, 1770,1690, 1610,1510, 1355,1165, 930,690 | 0.86(t),1.43,1.51, 1.64,3.91(1H,s), 4.09(2H,d),5.37 (2H,mult),5.85(1H, s),7.35(5H),9.05 (1H,mult) |
| 2 | CH$_3$<br>\|<br>—CH$_2$—CH$_2$C—CH$_3$<br>\|<br>CH$_3$ | 3350,2960, 1770,1690, 1612,1515, 1360,1163, 937,730,690 | 0.89(9H,s),1.45, 1.58,1.67,3.92 (1H,s),4.12(2H,t), 5.37(2H,mult), 5.88(1H,d),7.40 (5H),9.10(1H, broad) |
| 3 | CH$_3$<br>\|<br>—CH$_2$—C—CH$_2$CH⟨CH$_3$/CH$_3$<br>\|<br>CH$_3$ | 3350,2970, 1770,1690, 1610,1520, 1360,1165, 940,840,690 | 0.78,0.88,0.84(s), 1.05(d),1.37,1.45, 1.56,3.76(2H,s), 3.85(1H,s),5.35(2H, mult),5.83(1H,s), 7.35(5H),9.05(1H, mult) |
| 4 | —CH$_2$—CH(CH$_2$)$_3$CH$_3$<br>\|<br>CH$_2$(CH$_2$)$_2$CH$_3$ | 3400,2950, 1770,1685, 1613,1358, 1168,935,690 | 0.88(t),1.22(s), 1.43,1.52,1.62, 3.93(1H,s),4.10 (2H,d),5.40(2H, mult),5.93(1H,s), 7.45(5H),9.13(1H, broad) |

REFERENCE EXAMPLE 3

The penicillin compounds prepared by the methods of Reference Exanples were orally administered to rats (body weights : 200 ± 10 g.) in a dose of 200 mg/kg. as α-sulfobenzylpenicillin disodium salt. The urine excreted during the 15 hours following the administration was collected and the percent urinary recovery of α-sulfobenzylpenicillin disodium salt was determined. The results are set forth below. The quantitative determination of α-sulfobenzylpenicillin disodium salt was performed using *Pseudomonas aeruginosa* NCTC 10490.

As a control, the same amount of α-sulfobenzylpenicillin disodium salt was administered also by the oral route.

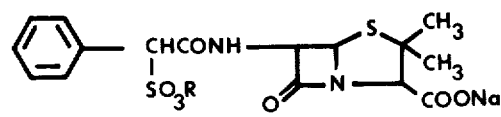

| R | Urinary recovery (%)<br>n stands for the number of rats used |
|---|---|
| —CH$_2$—CHCH$_2$CH$_3$<br>\|<br>CH$_2$CH$_3$ | 6.9 (n=6) |
| CH$_3$<br>\|<br>—CH$_2$—C—CH$_2$CH⟨CH$_3$/CH$_3$<br>\|<br>CH$_3$ | 5.1 (n=5) |

-continued

| R | Urinary recovery (%)<br>n stands for the number of rats used |
|---|---|
| 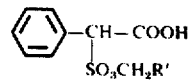 | 6.1 (n=6) |
| α-Sulfobenzylpenicillin disodium salt | 0.4 (n=6) |

What is claimed is:

1. α-Isobutylsulfophenylacetic acid.
2. An α-sulfophenylacetic acid derivative of the general formula:

$$\text{C}_6\text{H}_5\text{—CH—COOH}$$
$$\quad\quad\quad\quad\;\; |$$
$$\quad\quad\quad\quad\;\; \text{SO}_3\text{CH}_2\text{R}'$$

wherein R' is a branched alkyl group of 4 to 14 carbon atoms.

3. An α-sulfophenylacetic acid derivative as claimed in claim 2, wherein R' is 1-ethylpropyl.
4. An α-sulfophenylacetic acid derivative as claimed in claim 2, wherein R' is 2-methylpropyl.
5. An α-sulfophenylacetic acid derivative as claimed in claim 2, wherein R' is 2,2-dimethylpropyl.
6. An α-sulfophenylacetic acid derivative as claimed in claim 2, wherein R' is 1-butylpentyl.
7. An α-sulfophenylacetic acid derivative as claimed in claim 2, wherein R' is 1,1,3-trimethylbutyl.

* * * * *